United States Patent [19]

Streisinger

[11] 4,407,301

[45] Oct. 4, 1983

[54] DISC MEMBRANE CATHETER FOR PERFORMING CYSTOMETROGRAMS AND URETHRAL PROFILES

[75] Inventor: Erwin Streisinger, Maplewood, N.J.

[73] Assignee: C. R. Bard, Inc., Murray Hill, N.J.

[21] Appl. No.: 228,984

[22] Filed: Jan. 27, 1981

[51] Int. Cl.³ .............................................. A61B 5/10
[52] U.S. Cl. .................................. 128/774; 604/100; 604/103
[58] Field of Search ..................... 128/748, 780, 349 B, 128/325, 673, 674, 675, 748, 774, 780, 778; 604/100, 103

[56] References Cited

U.S. PATENT DOCUMENTS

| | | | |
|---|---|---|---|
| 4,063,548 | 12/1977 | Klatt et al. | 128/748 |
| 4,114,603 | 9/1978 | Wilkinson | 128/748 |
| 4,177,815 | 12/1979 | Patel | 604/103 |
| 4,214,593 | 7/1980 | Imbruce et al. | 128/349 B |
| 4,301,811 | 11/1981 | Layton | 128/748 |

Primary Examiner—Richard J. Apley
Assistant Examiner—J. L. Kruter
Attorney, Agent, or Firm—Dennison, Meserole, Pollack & Scheiner

[57] ABSTRACT

A diagnostic catheter for use in performing cystometrograms and urethral pressure profile tests having a shaft of conventional elastomeric construction closed at the distal end and having a CMG port adjacent to this end. An inflation lumen extends to a second port which underlies a thin inflatable member secured to the shaft up to the edges of the second port so that when inflated, the member only expands outwardly over the area of the port. Back pressure readings may be taken during catheter removal for precise location of urethral obstructions.

14 Claims, 8 Drawing Figures

DISC MEMBRANE CATHETER FOR PERFORMING CYSTOMETROGRAMS AND URETHRAL PROFILES

BACKGROUND OF THE INVENTION

The present invention relates broadly to a diagnostic catheter utilized in urodynamic investigations to detect and to evaluate in quantitative terms constrictions that might exist along the urethral duct of a human or animal subject. The urethral pressure profile test is now commonly used in the assessment of urodynamic evaluation. This test is especially pertinent with respect to patients with incontinence or obstructive symptomatology. Usually a profile of urethral pressure may be obtained by the withdrawal of a pressure recording catheter from the bladder through the urethra. Several methods of profilometry exist including measurement of pressure inside of a balloon which traverses the urethra and also the measurement of the urethral pressure that is transmitted against a fluid or gas that is infused through a small catheter traversing the urethra. Utilizing the last technique, single and multi-channeled urodynamic catheters employ an open system in the sense that pressures are measured by passing a liquid or gas through the catheter and then out through one or more of the orifices. Depending on the size of the space between the catheter and the urethral wall, flow is restricted to a certain degree and pressure will vary as the catheter is withdrawn. Liquid or gas will keep flowing through and out during the entire procedure. Normally, water is infused at the rate of 2 cc/min. As the catheter enters the urethral canal, it registers a minimal rise in pressure at the level of the internal sphincter or bladder neck. Proceeding downward, pressure will increase and reach a peak generally at the midpoint of the urethra in the female and in the membranrous urethra in the male, and then it will progressively drop.

What are known in the art as membrane catheters are closed systems also used in obtaining urethral pressure profiles. Here, the liquid that enters the catheter under pressure serves to expand a thin balloon or elastic element which is located adjacent the end of the catheter. The fluid is captive in the balloon and cannot flow out of the catheter. Single or double membrane catheters are frequently used for recording such urethral pressure profiles. As they are manually or mechanically withdrawn from the bladder cavity, the balloons will traverse the entire length of the urethra and serve to transmit pressure through the liquid with which they are inflated back to a chart recorder or other type of recording device. Frequently, pressure profiles are obtained under various states of stress such as coughing or bearing down and voluntary contraction of muscles. It will be obvious that any internal obstruction such as a tumor or other constriction along the urethra will oppose the expansion of the elastic balloon element. The back pressure that is created is therefore measured and recorded as noted.

A comparison of these various methods of recording urethral pressure profile may be found in the paper of Schmidt et al. "Recording Urethral Pressure Profile, Comparison of Methods and Clinical Implications," Urology, October 1977, Vol. X, No. 4, pp. 390-7.

Another test that is frequently performed in urodynamic investigations is the cystometrogram (CMG). This is a test of detrusor muscle function and consists of distending the bladder with a known volume of a fluid or gas while recording the intravesical pressure. In performing this test, the bladder can be filled with either water, saline solution, air or carbon dioxide or the like. The medium can be instilled either through the urethra or suprapubically. In most cases, the medium is instilled through a double lumen catheter at a rate of approximately 10 cc/min. The catheter that is employed permits both filling of the bladder and recording of bladder pressure.

In a normal CMG test the filling phase looks at the bladder's ability to comply to increased volume. The detrusor muscle normally expands as volume increases so that the bladder initially rises very little in pressure to the time the patient voids. If bladder pressure continually rises during filling, it can be due to a number of factors which would bear further investigation. Another important observation during the filling phase of the CMG is any rise in bladder pressure that is not accompanied by rise in abdominal pressure. This represents detrusor contraction. The voiding phase of a CMG determines if detrusor reflex exists.

Frequently, CMG testing and urethral pressure profile tests are performed in sequence wherein the CMG test determines bladder capacity and pressure and subsequently a urethral pressure profile test is performed utilizing a membrane catheter.

An example of a urethral membrane catheter of the type known in the art today is the dual channel membrane catheter produced by Brown Corporation of Santa Barbara, Calif. This catheter is designed to profile the dynamic and/or static pressure of the urethra and a second channel is provided for simultaneously recording intravesical pressure while profiling the urethra. The catheter is constructed of silicone and is barium impregnated for X-ray detection. A membrane chamber is located approximately 8 cm from the distal end and when infused with carbon dioxide at controlled flow rates, serves to measure the total urethral resistance against the membrane. Static urethral pressure is measured by placing the membrane chamber at the point in the urethra where greatest resistance is measured while infusing the bladder with carbon dioxide on the second channel. It should be noted that the membrane of the type utilized in the Brown catheter and others well-known in the art are in the form of sleeves which expand to form a small balloon such as found in the conventional Foley catheter. Examples of Foley type catheters may be seen in U.S. Pat. Nos. 3,825,013 and 3,528,869.

The invention herein described is referred to as a disc membrane catheter and varies from the prior art in that the elastic elements are applied in the form of a thin silicone or other elastic disc which is applied over one or more small oblong openings in the catheter shaft. Application of internal pressure through the catheter causes these flat disc membranes to expand outwardly. Because they are dimensionally much smaller than the balloon membranes, the disc-type yields better resolution with respect to location of constrictions or obstructions along the urethra.

While in many measurement situations, the external resistant pressure is applied evenly, in some instances, and especially along the urethral duct, there may be an obstruction present in a small localized area only along one side of the urethra. A circular balloon type membrane would not be useful in detecting the orientation of such an obstruction. However, the disc membrane of the present invention normally responds to pressure averaged around the catheter. When a discontinuity is present, however, its location can be detected by rotating the catheter between forward and backward passes. In this respect, the disc membrane is much more versatile than the balloon type described above.

An important advantage of the disc membrane catheter over the conventional membrane type is its relative freedom from entrapped air bubbles. During the filling process the conventional balloon type membrane invariably will trap large air bubbles in the expanding balloon. Such air bubbles being compressible interfere with the accuracy of the pressure readings when the catheter is in use. Elaborate and time consuming procedures are required to dislodge the bubbles and avoiding them is nearly impossible. The disc membrane catheter's basic geometry is such that it does not provide large corners in which the air bubbles can remain lodged.

SUMMARY AND OBJECTS OF THE INVENTION

A new urodynamic diagnostic catheter is provided utilizing a relatively small inflatable disc section connected by means of a lumen through which fluid under some pressure may be applied for the purpose of inflating the disc and for transmitting pressure back to a recorder as the catheter is rotated and/or moved longitudinally within the urethra. The catheter may also be constructed with an additional lumen for inflow of a gas or liquid which may be utilized in a cystometrogram.

It is a primary object of the present invention to provide a membrane catheter of the disc type for improved results in performing urethral pressure profile investigations.

It is a further object of the invention to provide in a unitary assembly a membrane catheter of the disc type for urethral pressure profile testing (UPP) and also a cystometrogram channel for influx of liquid or gas into the bladder.

A further object is to provide a urinary diagnostic catheter assembly which may be easily and inexpensively manufactured from silicone materials and which may be interchangeably used in sequence for both UPP and CMG tests.

Various other objects and advantages of my invention will be readily apparent from the following detailed description taken in conjunction with the drawings in which an exemplary embodiment of the invention and two modifications are shown.

DETAILED DESCRIPTION OF THE DRAWINGS

Figure 1:
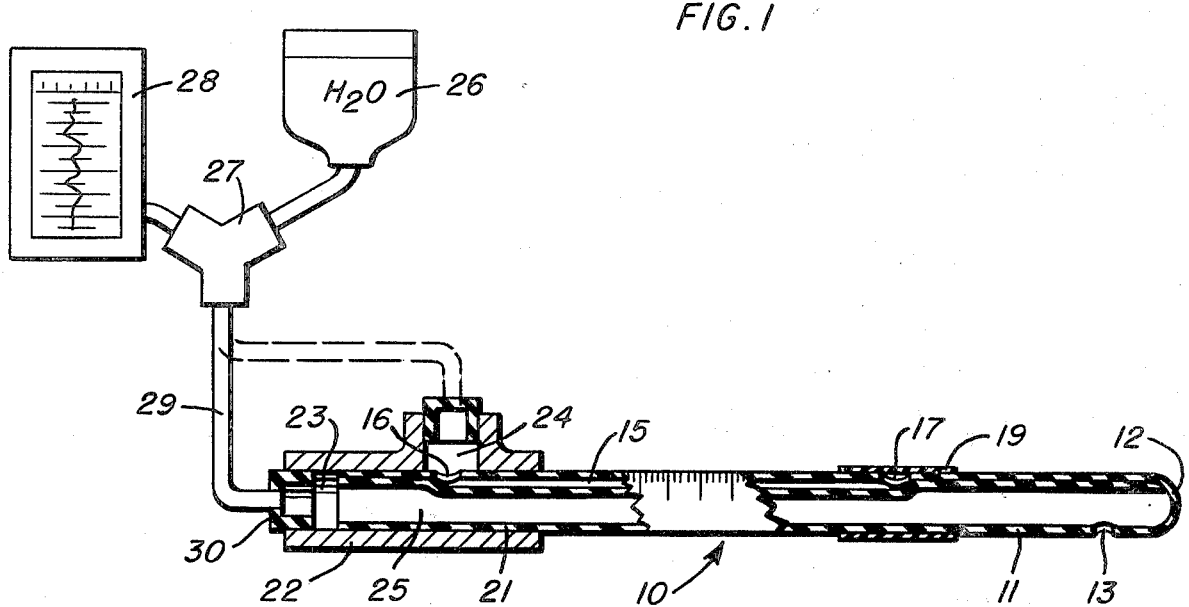
FIG. 1 is a longitudinal section through the preferred embodiment of the disc membrane catheter with the central portion being shown in full and connected for CMG measurement with connection for UPP test shown in dotted lines.

Referring now to the drawings wherein like elements are assigned identical reference characters, the catheter forming the invention is shown generally at 10 and consists of an elongated flexible tubular shaft 11 which is preferably formed of silicone material. Any conventional catheter material such as non-toxic plastic, as for example polyvinylchloride and copolymers thereof, could also be used as well as latex, polyvinyl acetate, and the like. The catheter shaft is formed with a rounded tip 12 and a generally circular port 13 is formed on the shaft spaced a short distance proximally from the tip. This outlet port 13 is used in the CMG routine. The catheter is extruded or otherwise formed with a lumen 15 which serves as the inflation passageway. An inflation inlet port 16 is provided adjacent the proximal end of the lumen 15 and an outlet port or eye 17 is formed in the catheter shaft wall near the distal end of the lumen 15. Eye 17 may be round or oblong as desired. The inflation port having a width dimension transverse to the longitudinal axis of the catheter equal to the width of the inflation lumen.

Figure 2:
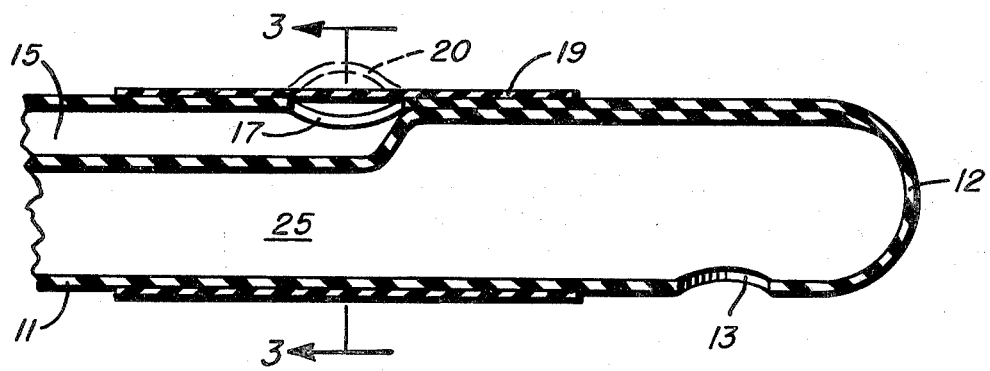
FIG. 2 is an enlarged sectional view of the tip of the catheter shown in FIG. 1 with the inflated disc shown in dotted lines.

In the form of the invention shown in FIG. 1, a thin silicone sleeve 19 is secured about the shaft 11 as shown best in FIG. 2. It is essential that the sleeve is securely adhered to the body of the shaft throughout its circumference so that the only area unattached to the shaft is immediately adjacent and overlying the inflation outlet port 17. This will ensure that during inflation only a very small area adjacent the outlet port will expand. The dotted line showing in FIG. 2 indicates the inflated portion 20 when under pressure.

The proximal portion of the catheter shown at 21 is received within a plastic fitting 22 which permits attachment of various plugs for connection as later described herein. A CMG port is provided in the fitting as at 23 and a UPP inflation port is provided as at 24. It will be noted that the port 24 is immediately adjacent the inflation inlet port 16 and that the port 23 communicates with the main chamber of the catheter 25. Externally of the catheter, a source of fluid such as sterile water is shown at 26 and this is connected by means of a Y-connector 27 and a tube 29 to an adapter member 30 received in the end of the fitting 22 and in connection with the CMG port. A pressure transducer, with a chart recorder, CRT screen, or any other type of conventional recording means is provided as at 28 and is connected to the remaining leg of the Y-connector 27. It will be appreciated that in use the liquid shown at 26 is injected or otherwise forced through the line or tube 29 into the main body 25 of the catheter where it will pass outwardly through the CMG outlet port 13 into the urethra. Back pressure will be recorded through the same passageway on the recorder 28.

When the device is used for urethral pressure profile (UPP) tests, the tube 29 and the adapter 30 are connected adjacent to the UPP inflation port 24 as shown in dotted lines in FIG. 1. Thereafter, liquid or carbon dioxide or other gas may be injected from the source 26 through the Y-connector 27, the tube 29, and the inflation port 24, into the inflation lumen 15 wherein the liquid or gas will flow outwardly through the port 17 and will serve to inflate the sleeve 19 as shown at 20.

Figure 4:
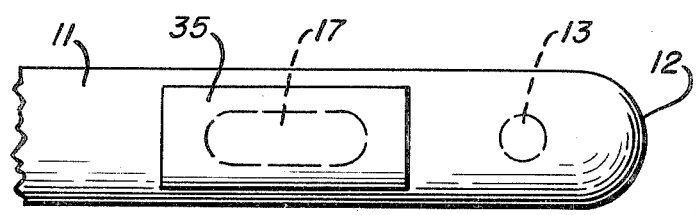
FIG. 4 is a top view of a catheter using a modified form of disc.

In the modified form of the invention shown in FIG. 4, the sleeve 19 is replaced by a rectangular disc form or patch shown at 35. Here again, like sleeve 19, the patch 35 is formed of thin latex or silicone material and is secured immediately adjacent the inflation outlet port 17 so that the only area unsecured is directly over the outlet port. It is essential to note that the disc attachment extends all the way to the peripheral edge of the eye or outlet port 17. Here eye 17 is shown as oblong.

Figure 3:
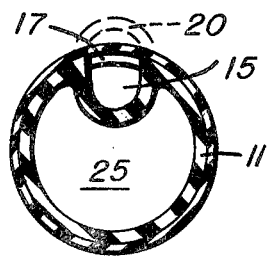
FIG. 3 is a section taken along lines 3—3 of FIG. 2.
Figure 5:
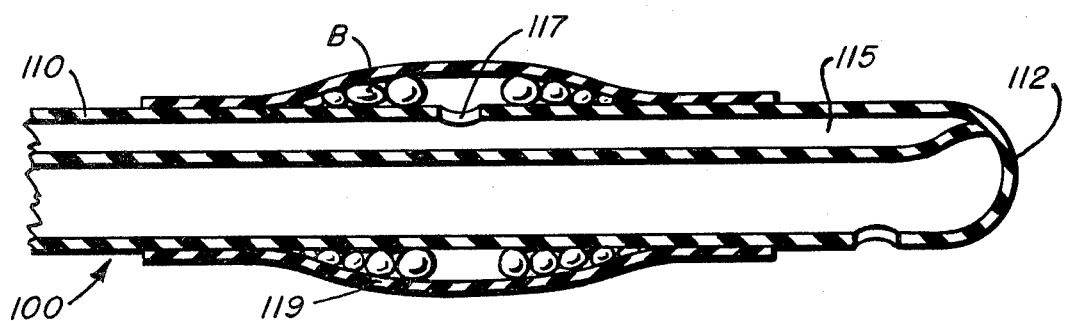
FIG. 5 is a longitudinal section through the known prior art type of membrane catheter showing the accumulation of air bubbles.

A typical prior art membrane catheter is shown in FIG. 5 at 100 and includes a shaft 110 having a rounded tip 112 thereon. The inflation lumen is designated as 115 and has the conventional outlet port or eye 117. A sleeve 119 also formed of silicone or the same material as the catheter shaft is secured to the shaft adjacent its proximal and distal edges, however the entire circumferential portion which overlies the outlet port 117 and continues around for 360° is free of the shaft so that air or liquid passed into the inflation lumen 115 will serve to expand the entire sleeve as shown in FIG. 5. In effect, a circumferential balloon is provided. The problem with this type of device is that it serves to entrap air bubbles shown at B which cause inaccurate readings in use. With the catheter of the present invention, no appreciable air entrapment can occur. It is virtually impossible to fill the prior art type of balloon or membrane catheter without trapping large air bubbles as shown. The presence of the air bubbles which are compressible interferes with the accuracy of the pressure readings when the catheter is used and elaborate and time procedures are necessary for dislodging the bubbles. A comparison with the arrangement shown in FIGS. 2 and 3 will clearly indicate that in my disc membrane catheter large corners are not present in which air bubbles can remain lodged.

It is also possible to form a disc membrane catheter by immersion and slow withdrawal of the catheter from a silicone solution formed of proper consistency to result in the formation of a thin film on the opening 17 which is cut into the catheter shaft. When dried this film serves to become the membrane.

Figure 6:
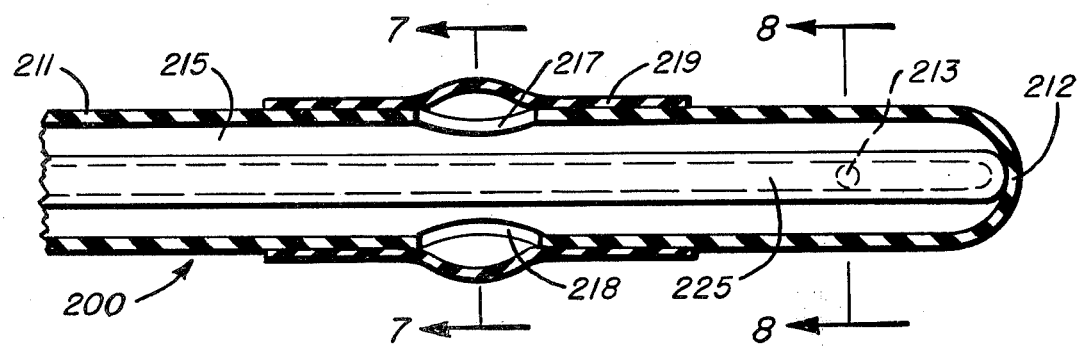
FIG. 6 is a modified form of the invention shown in longitudinal section utilizing opposed openings.
Figure 7:
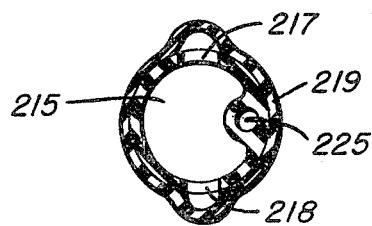
FIG. 7 is a cross-section taken along lines 7—7 of FIG. 6.
Figure 8:
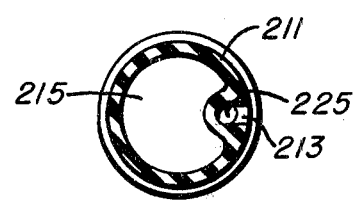
FIG. 8 is a section taken through lines 8—8 of FIG. 6.

A further modification of the basic invention is shown in FIG. 6 wherein the provision of two inflatable areas is considered. The catheter 200 in FIG. 6 utilizes multiple inflated discs and includes a main shaft 211 formed with a rounded tip 212. A CMG lumen 225 extends along the inner wall of the catheter as shown best in FIG. 7 and is provided at 213 with an outlet port. The inflation lumen in this modification forms the main chamber of the catheter and is shown at 215. A plurality of outlet ports 217 and 218 are shown and in the embodiment herein depicted two such ports are disclosed although it is indeed possible to have three or even more if required. A sleeve 219 is secured to the catheter 211 in the same manner that the sleeve 19 is applied to the catheter shaft 11 in the FIG. 2 embodiment. When appropriate gas or liquid is inserted into the catheter inflation lumen 215, the sleeve will expand immediately adjacent the outlet openings 217 and 218 as shown in FIGS. 6 and 7. Entrapment of an air pocket between ports 217, 218 and catheter tip 212 can be readily avoided by initial filling of the catheter in a vertical position, tip 212 being at the bottom. The CMG lumen and port 213 are used in the same manner as depicted in FIGS. 1 and 2.

As shown in FIG. 1, indicia may be provided along the catheter shaft for aid in placement and in location of obstructions as the catheter is withdrawn.

I claim:

1. A diagnostic catheter for performing cystometrogram (CMG) and urethral pressure profile tests comprising a hollow shaft having a proximal end and a distal end, the distal end being closed, a CMG port in the shaft wall adjacent said distal end in communication with the proximal end of the shaft, an inflation outlet port in said shaft wall, an inflation lumen extending inside said shaft from said inflation outlet port to the proximal end of the shaft, a thin inflatable elastomeric member means located on the outside of said shaft and overlying said inflation outlet port and secured to said shaft about the periphery of said inflation outlet port and said means expandable outwardly only in the localized area proximal of said outlet port, and means for injection of fluid alternatively into the proximal end of the inflation lumen or to the CMG port, and means for measuring the back pressure from the same.

2. A catheter as defined in claim 1, wherein said elastomeric means is a sleeve secured completely about the catheter shaft.

3. A catheter as defined in claim 1, wherein said elastomeric member means consists of a generally rectangular patch.

4. A catheter as defined in claim 1 and further includng at least one additional inflation outlet port in said shaft in communication with said inflation lumen, said elastomeric member overlying all of said outlet ports and being secured to said shaft about the peripheries of said outlet ports.

5. A catheter as defined in claim 4, wherein a lumen is formed on the interior side wall of the shaft communicating from said CMG port to the proximal end of the shaft.

6. A catheter as defined in claim 1, wherein said inflation outlet port is of oblong configuration.

7. A catheter as defined in claim 1, wherein said inflation outlet port is proximal of said CMG port.

8. A catheter as defined in claim 1, and further including a tubular fitting on the proximal end of said shaft and having connector means therein for connection to said means for injection of fluid and for recording the back pressure.

9. A catheter as defined in claim 8, wherein said means for recording the back pressure is a chart recorder.

10. A catheter as defined in claim 8 wherein said means for injection of fluid includes a fluid reservoir, and a Y-connector means having a conduit extending therefrom and terminating in a plug means adapted for connection to said connector means, said reservoir and said means for recording the back pressure being connected to said Y-connector means.

11. A diagnostic catheter comprising a hollow shaft formed of elastomeric material and having a main lumen and at least one inflation lumen therein, the distal end of said shaft being closed and said inflation lumen extending to the proximal end of said shaft, an inflation port in the wall of said shaft and flush with the exterior surface thereof and located adjacent to the distal end and being in communication with said inflation lumen, said inflation port having a width dimension transverse to the longitudinal axis of the catheter equal to the width of the inflation lumen and a thin inflatable elastomeric member means secured firmly to said shaft and overlying said inflation port, and secured completely there about the area of securement of the inflatable member extending to the edges of said port so that the area of inflation is localized proximate to the area of the port only.

12. A catheter as defined in claim 11 wherein said port is of oblong shape.

13. A catheter as defined in claim 11 wherein the inflatable member means is a circumferential sheath.

14. A catheter as defined in claim 11 wherein said inflatable member means is of generally rectangular shape positioned lengthwise along the shaft.

* * * * *